(12) United States Patent
Voinalovich

(10) Patent No.: US 6,633,372 B2
(45) Date of Patent: Oct. 14, 2003

(54) METHOD FOR INSPECTION OF AN ANALYZED SURFACE AND SURFACE SCANNING ANALYZER

(75) Inventor: Alexandr Vladimirovich Voinalovich, Zelenograd (RU)

(73) Assignee: Obschestvo S Ogranichennoi Otvetstvennostiju "Reflex Lait", Moscow (RU)

( * ) Notice: Subject to any disclaimer, the term of this patent is extended or adjusted under 35 U.S.C. 154(b) by 0 days.

(21) Appl. No.: 09/866,725

(22) Filed: May 30, 2001

(65) Prior Publication Data

US 2002/0005943 A1 Jan. 17, 2002

Related U.S. Application Data

(63) Continuation of application No. PCT/RU99/00328, filed on Sep. 8, 1999.

(30) Foreign Application Priority Data

Nov. 30, 1998 (RU) ............................................. 98121268

(51) Int. Cl.⁷ .............................................. G01N 21/00
(52) U.S. Cl. ........................ 356/73; 356/237.5; 250/234
(58) Field of Search ............................. 356/73, 237.1, 356/445, 426; 250/234, 236, 559.01, 559.4, 559.41, 559.44

(56) References Cited

U.S. PATENT DOCUMENTS

| | | | |
|---|---|---|---|
| 4,314,763 A | 2/1982 | Steigmeier et al. | 356/237 |
| 4,655,592 A | 4/1987 | Allemand | 356/237 |
| 5,377,001 A | 12/1994 | Malin et al. | 356/237 |
| 5,377,002 A | 12/1994 | Malin et al. | 356/237 |
| 5,420,689 A * | 5/1995 | Siu | 356/394 |
| 6,271,916 B1 * | 8/2001 | Marxer et al. | 356/237.3 |

FOREIGN PATENT DOCUMENTS

| | | | |
|---|---|---|---|
| DE | 3626724 | 2/1988 | |
| EP | 0 398 781 A2 | 11/1990 | |
| JP | 3-163338 | 7/1991 | |
| RU | 1786406 | 1/1993 | |
| RU | 2064670 | 7/1996 | |
| RU | 2141647 | 11/1998 | |
| WO | WO 97/12226 * | 3/1997 | G01N/21/47 |

OTHER PUBLICATIONS

Copy of IEPR and English translation of pp. 3 and 4 of IEPR..
Copy of International Search Report.
Altendorfer et al., H., "Unpatterned surface inspection for next–generation devices", Solid State Technology, Aug. 1996, vol. 39, No. 8, pp. 93, 95, 96 and 99.

* cited by examiner

Primary Examiner—Kevin Pyo
Assistant Examiner—Seung C. Sohn
(74) Attorney, Agent, or Firm—Ladas & Parry

(57) ABSTRACT

The invention relates to optical instruments. There are provided a method for inspection of an analyzed surface and a scanning analyzer for inspection of defects on the surface. The method comprises the steps of rotating an object with the analyzed surface about a first center of rotation; forming a light spot on the analyzed surface; and sensing separately a light mirror-reflected and a light scattered from the analyzed surface at the incidence point of the light spot; and detecting surface defects by analyzing the produced signals. To implement the method, a surface scanning analyzer moves the light spot relative to the analyzed surface through an arc about a second center of rotation which lies outside the analyzed surface; and detects defects on the surface of wafers by measuring the magnitude of the scattered light. The reduced size and cost of the measurement device enables its integration into manufacturing equipment for inspection of semiconductor wafers in electronic industry.

18 Claims, 4 Drawing Sheets

US 6,633,372 B2

METHOD FOR INSPECTION OF AN ANALYZED SURFACE AND SURFACE SCANNING ANALYZER

This application is a continuation of application PCT/RU99/00328 filed Sep. 8, 1999, the benefit of which is claimed under 35 USC 120.

FIELD OF THE INVENTION

The present invention relates to optical instruments and can be particularly used to develop new and improve existing devices for analysis of a surface of semiconductor wafers, and to integrate the devices into the manufacturing equipment, as well as to examine the uniformity degree of a surface of other articles.

BACKGROUND OF THE INVENTION

During the manufacture of semiconductor devices, no dust particles and other defects can be tolerated on the surface of semiconductor wafers. It is desirable to reveal such defects as early as possible to remove at once a source of their origin. To solve this problem a method is widely used utilizing the known fact that any particle on a smooth surface, or a surface defect scatters the light incident onto the surface.

For example, a method for inspection of an analyzed surface is known from U.S. Pat. No. 4,314,763 (Int.Cl. G 01 N 21/88, 09.02.82), comprising the steps of: rotating the analyzed surface about a center of rotation, forming a light spot on the analyzed surface, and sensing a light scattered from the analyzed surface using an optical system.

The same U.S. Pat. No. 4,314,763 discloses a surface scanning analyzer comprising: a light source for illuminating an analyzed surface by a light spot at an angle close to the normal to the analyzed surface; a photodetector for sensing the light scattered from the analyzed surface; and a rotary table for mounting and rotating an article with the analyzed surface thereon about an axis of revolution parallel to the normal to the analyzed surface.

In the analyzer implementing the above method, the rotated analyzed surface is being moved along a straight line relative to a point at which the light spot is formed on the surface. This is the shortage of the method and the analyzer implementing the method since it is necessary to provide movement of a large object, i.e. the rotary table for mounting a semiconductor wafer (up to 300 mm in diameter), equipped with a rotation actuator, which leads to increased size and cost of the device.

The closest prior art is a method for inspection of an analyzed surface comprising the steps of rotating an object having the analyzed surface about a first center of rotation; forming a light spot on the analyzed surface sensing a light scattered from the analyzed surface at the incidence point of the light spot (Altendorfer H. et al. <<Unpatterned surface inspection for next-generation devices>>.—Solid State Technology, 1996, v. 39, № 8, pp. 93–97).

The same reference discloses a surface scanning analyzer comprising: a rotary table for mounting and rotating an object with an analyzed surface about a first axis of revolution that is perpendicular to the analyzed surface; a light source for illuminating the analyzed surface by a light spot at an angle close to the normal to the analyzed surface; a collecting mirror in the form of a truncated body of revolution formed by revolving an ellipse about a second axis of revolution which is parallel to the first axis of revolution and substantially coincides with the normal to the analyzed surface erected at the incidence point of said light spot, said incidence point being at the focus of said truncated body of revolution, a first section plane of the body of revolution being perpendicular to the second axis of revolution in the immediate proximity to said focus, and a second section plane being parallel to the first section plane; a photodetector for sensing the light scattered from the analyzed surface and reflected from the collecting mirror.

In this method a progressive movement of the rotated analyzed surface is remained, i.e. as before it is necessary to move a massive object, which results, as mentioned before, in increased size and cost of the device, hampering substantially integration of the device into the process equipment.

Recent developments of a cluster type equipment in the semiconductor industry have enabled several operations to be carried out simultaneously and ensured the cleanness grade infeasible with conventional equipment. The appearance of new process equipment poses the problem to develop a new measurement equipment capable of operating in the cluster process conditions. The demands imposed on such devices differ significantly from the demands placed on conventional devices. One of the most important requirements is a minimal size of the device, which is dictated by a small volume of clean environment inside the cluster. module. Since the cluster measurement devices are integrated into each individual module, they must be also manufactured and serviced at a low cost.

Thus, the object of this invention is to develop such methods for inspection of an analyzed surface, and a surface scanning analyzer that would be free from the indicated drawbacks.

SUMMARY OF THE INVENTION

The above object and the indicated technical result of the present invention are achieved in the following manner.

In one aspect, the invention relates to a method for inspection of an analyzed surface, comprising the steps of: rotating an object having the analyzed surface about a first center of rotation; forming a light spot on the analyzed surface; sensing separately a light mirror-reflected and a light scattered from the analyzed surface at the incidence point of the light spot, wherein in accordance with the present invention, the method includes the steps of: moving the light spot relative to the analyzed surface through an arc about a second center of rotation which lies outside the analyzed surface; and aligning, at least in one predetermined position, the light spot having an elongated form on the analyzed surface with its maximum size along a radius extending from the first center of rotation through the light spot.

A feature of this method is that in the predetermined position the light spot is located substantially in the middle of said analyzed surface radius extending from the first center of rotation, or the light spot, during its movement through said arc, is turned so as to retain its alignment along the radius extending from the first center of rotation thought the light spot all along the scanning line.

One more feature of this method is that the light scattered from the analyzed surface is collected using a system of mirrors, wherein one of the mirrors is in the form of a truncated ellipsoid of revolution having one axis of revolution substantially coinciding with the normal to the analyzed surface erected at the incidence point of said light spot, said incidence point being at a first focus of said truncated ellipsoid of revolution, a first section plane of the ellipsoid being located perpendicularly to its axis of revolution in the immediate proximity to said first focus, and a second section plane being parallel to the first section plane, and another mirror is a flat mirror having an aperture at the center, arranged at an angle to the axis of revolution of the truncated ellipsoid of revolution, and intended for passing therethrough the light from the light source to the analyzed surface and the light mirror-reflected therefrom, and for reflecting the light scattered from the analyzed surface and reflected from the collecting mirror, wherein the light reflected from the flat mirror is passed through a light filter and then diaphragmed at a point corresponding to the second focus of said ellipsoid of revolution with regard of reflection from said flat mirror.

In one embodiment of the method, the light scattered from the analyzed surface is collected using a system of mirrors, wherein one of the mirrors is in the form of a truncated paraboloid of revolution having an axis of revolution substantially coinciding with the normal to the analyzed surface erected at its incidence point of said light spot, said incidence point being at the focus of said truncated paraboloid of revolution, a first section plane of the paraboloid being located perpendicularly to the axis of revolution in the immediate proximity to said focus, and a second section plane being parallel to the first section plane, and another mirror is a flat mirror having an aperture at the center, arranged at an angle to the axis of revolution of the truncated paraboloid of revolution, and intended for passing therethrough the light from the light source to the analyzed surface and the light mirror-reflected therefrom and for reflecting the light scattered from the analyzed surface and reflected from the collecting mirror, wherein the light reflected from the flat mirror is passed through a light filter, collected by a lens and then diaphragmed.

In another aspect, the present invention relates to a surface scanning analyzer comprising: a rotary table for mounting thereon an object with an analyzed surface, and rotating the same about a first axis of revolution that is perpendicular to the analyzed surface; a light source for illuminating the analyzed surface by a light spot at an angle close to the normal to the analyzed surface; a collecting mirror in the form of a truncated body of revolution formed by revolving a second order curve about a second axis of revolution which is parallel to the first axis of revolution and substantially coincides with the normal to the analyzed surface erected at the incidence point of said light spot, said incidence point being at the focus of said truncated body of revolution having a first section plane perpendicular to the second axis of revolution in the immediate proximity to said focus, and a second section plane parallel to the first section plane; a first light sensing unit for sensing the light mirror-reflected from the analyzed surface, located close to the light source; a second light sensing unit for sensing the light scattered from the analyzed surface and reflected from the collecting mirror; a flat mirror having an aperture at the center, arranged at an angle to the axis of revolution of the truncated body and intended for passing therethrough the light from the light source to the analyzed surface and the light mirror-reflected therefrom to the first light sensing unit and for reflecting the light from the collecting mirror to the second light sensing unit, wherein in accordance with the present invention, the light source, the collecting mirror, the flat mirror with the aperture, and the first and second light sensing units are accommodated in a housing rotatable about a third axis of revolution which is parallel to the first axis of revolution and passes outside the object with the analyzed surface and/or the rotary table; the light source is mounted so as said light spot having an elongated form on the analyzed surface is aligned, at least in one predetermined position, with its maximum size along a radius extending from the first center of rotation through the light spot.

A feature of this analyzer is that the first light sensing unit is a light absorber or a photodetector to determine the presence of non-scattering defects on the analyzed surface.

Another feature of this analyzer is that the second light sensing unit is intended for sensing the light reflected from the flat mirror.

One more feature of this analyzer is that the body of revolution of the collecting mirror is an ellipsoid of revolution having a diaphragm placed at the second focus with regard of reflection from the flat mirror, for passing through the diaphragm the light reflected from the flat mirror to the second light sensing unit. In this case, a light filter may be mounted between the flat mirror and the diaphragm.

A feature of another embodiment is that the body of revolution of the collecting mirror is a paraboloid of revolution, and a collecting lens and a diaphragm may be mounted between the flat mirror and the second light sensing unit, for collecting and passing the light reflected from the flat mirror to the second light sensing unit. In this case, a light filter may mounted between the flat mirror and the collecting lens.

One more feature of the analyzer is that it further comprises a housing rotation actuator to enable movement of the housing over the analyzed surface at least to one side from the center of rotation.

Yet one more feature of the analyzer is that in said predetermined position of the housing, said light spot is located substantially in the middle of said analyzed surface radius extending from the center of rotation of the surface, or in that the housing rotation actuator is provided with housing rotation angle measurement means, and the light source is provided with position correction means for turning the light source in accordance with signals from the rotation angle measurement means to enable said aligning of the light spot along the radius extending from the center of rotation of the analyzed surface all along the scanning line.

Yet one more feature of the analyzer is that the housing is light-absorbing on the inside.

At last, one more feature of the analyzer is that the rotary table is provided with three suction cups located symmetrically about the first axis of revolution and intended for mounting the object with the analyzed surface on the rotary table.

No objects of the same purpose as the claimed ones, which would possess all of the aforementioned features of the subject matters of the present invention, have been revealed in the background art. Thus, the method for inspection of an analyzed surface and the surface scanning analyzer in accordance with the present invention may be considered novel.

Subject matters of the same purpose as the claimed ones are known, which comprise individual features similar to the main features of the claimed method and analyzer. For example, in U.S. Pat. Nos. 5,377,001 and 5,377,002 (Int.Cl. G 01 N 21/00, 27.12.94), the light spot is shown on the analyzed surface (FIG. 7a in each of these patents) in an elongated form along the radius extending from the center of rotation of the analyzed surface; however, the specifications to the patents lack any explanations as to how the spot should be arranged throughout the scanning line. Moving the analyzed surface in two mutually perpendicular directions is disclosed in EP Application N° 0398781, Int.Cl G 01 N 21/88, 22.11.90. Linear movement of the assembly with the light source and a light sensing unit over the rotary analyzed surface is known from Japan Unexamined Application No. 03-163338 (Int.Cl. G 01 N 21/88, 15.07.91). The use of a rotary housing in the form of the tone arm is known as such in disk turntables. RU Patent No. 2064670 (Int.Cl. G 01 N 21/47, 27.07.96) teaches the use of the collecting mirror in the form of the ellipsoid of revolution. However, no information is available in the background art on the use of a rotary housing for placing therein optical elements to illuminate the analyzed surface and sense light fluxes mirrored and scattered therefrom, as well as information on how the light spot must be just aligned on the analyzed surface. Thus, the subject matters of the present invention may be considered involving the inventive step.

BRIEF DESCRIPTION OF THE DRAWINGS

The invention will become apparent from the following description of the preferred embodiment of the claimed analyzer for implementing the claimed method with reference to the accompanying drawings, in which:

DETAILED DESCRIPTION OF THE PREFERRED EMBODIMENT

A method for inspection of an analyzed surface according to the present invention may be implemented using a scanning analyzer made in accordance with the present invention, an example of which is shown in the attached drawings.

Figure 1:
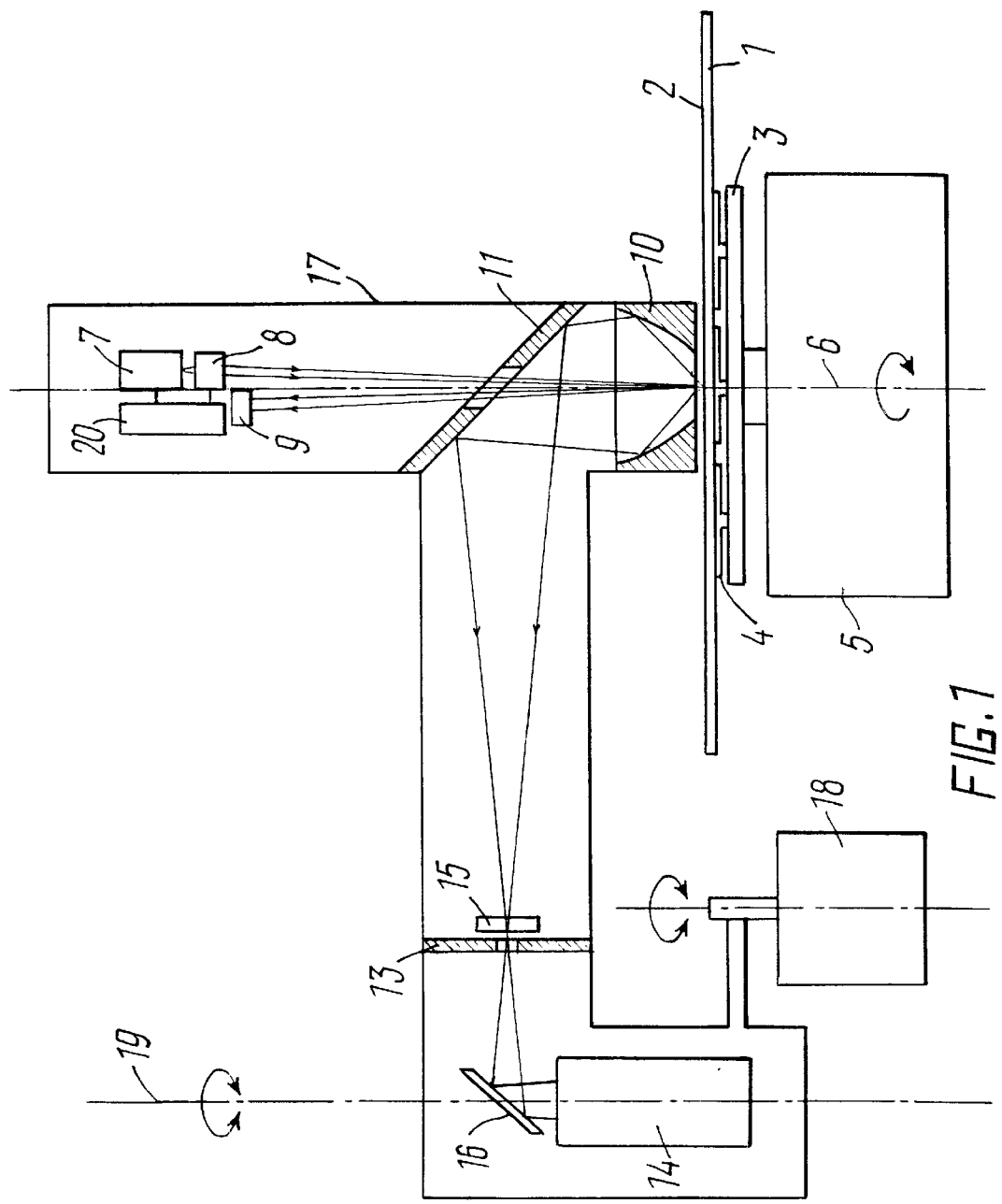
FIG. 1 illustrates a schematic diagram of an embodiment of the optical and mechanical part of the surface scanning analyzer in accordance with the present invention.

FIG. 1 shows a schematic diagram of the optical and mechanical part of the surface scanning analyzer in accordance with the present invention. An object 1 with an analyzed surface 2 is mounted on a rotary table 3 which is provided with suction cups 4. In use of the analyzer according to the present invention for inspection of a surface while manufacturing semiconductor wafers, the suction cups are located symmetrically about the center of rotation of the rotary table 3, i.e. spaced apart at 120° through an arc about its center of rotation. The rotary table 3 has a revolution motor 5 (particularly, a stepper) to revolve the rotary table about a first axis 6 of revolution.

As mentioned above, the present invention utilizes the known fact that defects on the smooth surface scatter the incident light sideways when said surface is illuminated with a light beam in the direction close to the normal to this surface.

For this purpose, the analyzed surface 2 is illuminated by a light source 7 which may comprise a semiconductor laser. The light from the source 7 is collected and focused with a lens 8 into a spot on the analyzed surface 2. The light source 7 with the lens 8 is disposed over the object 1 mounted on the rotary table 3, so that the light beam toward the analyzed surface 2 has a direction close to the normal to this surface. (In FIG. 1 the normal to the analyzed surface 2 at the point of incidence of the light beam from the light source 7 coincides with the first axis of revolution 6, this is done only to make understanding of the present invention more easy). A first light sensing unit 9 is disposed near the light source 7 to sense the light mirrored from the analyzed surface 2.

The first light sensing unit 9 may be merely an absorber which prevents reflection of the light mirror-reflected from the analyzed surface 2 back to it. However, this unit being a photodetector 9 may sense the light mirror-reflected from the analyzed surface 2 in order to determine the presence of non-scattering defects of different types on the surface of the studied object 1 (for example, a semiconductor wafer) from a variation of the intensity of the light mirror-reflected from the analyzed surface 2.

The light scattered from defects present on the analyzed surface 2 (for example, dust particles on the surface of a semiconductor wafer, defects in the subsurface area, the surface relief) may be directed to different sides at angles different from the normal to the analyzed surface 2. In order to use this scattered light in analysis, a collecting mirror 10 is employed made in the form of a body of revolution formed by revolving a second order curve about a second axis of revolution which is parallel to the first axis of revolution and substantially coincides with the normal to the analyzed surface erected at the incidence point of said light spot. (In FIG. 1 the second axis of revolution coincides with the first axis of revolution 6, but this is done only to improve understanding of the present invention.) The second order curve may be either an ellipse or parabola, one focus of the ellipse or the focus of the parabola coinciding with the incidence point of the light from the source 7 onto the analyzed surface 2. To ensure this, the body of revolution is made truncated, a first section plane being located perpendicularly to the second axis of revolution in the immediate proximity to said focus, and a second section plane of the body of revolution being parallel to the first section plane. A so formed gap between the edge of the collecting mirror 10 located in the first section plane, and the analyzed surface 2 enables free motion of the collecting mirror 10 over the analyzed surface 2. The light scattered from defects on the analyzed surface falls onto the inner reflecting surface of the collecting mirror 10 and is reflected aside from the analyzed surface 2 either parallel to its normal in the case of parabolic shape of the mirror 10, or to the point of the other focus in the case of elliptical shape of the collecting mirror 10.

In order to separate the light scattered from defects from the mirror-reflected light, the present invention uses a flat mirror 11 with an aperture in its center, which is mounted at an angle to the normal to the analyzed surface 2 (to the second axis of revolution about which the above mentioned second order curve, paraboloid or ellipse, is revolved). This angle in FIG. 1 is 45°, but it may have another value if necessary. The aperture in the center of the flat mirror 11 enables an unimpeded transmission of the light from the light source 7 to the analyzed surface 2, and the mirror reflection from it to the first light sensing unit 9. At the same time, the flat mirror 11 reflects the light collected and reflected from the collecting mirror 10 aside from the direction of propagation of the light from the source 7.

Figure 2:
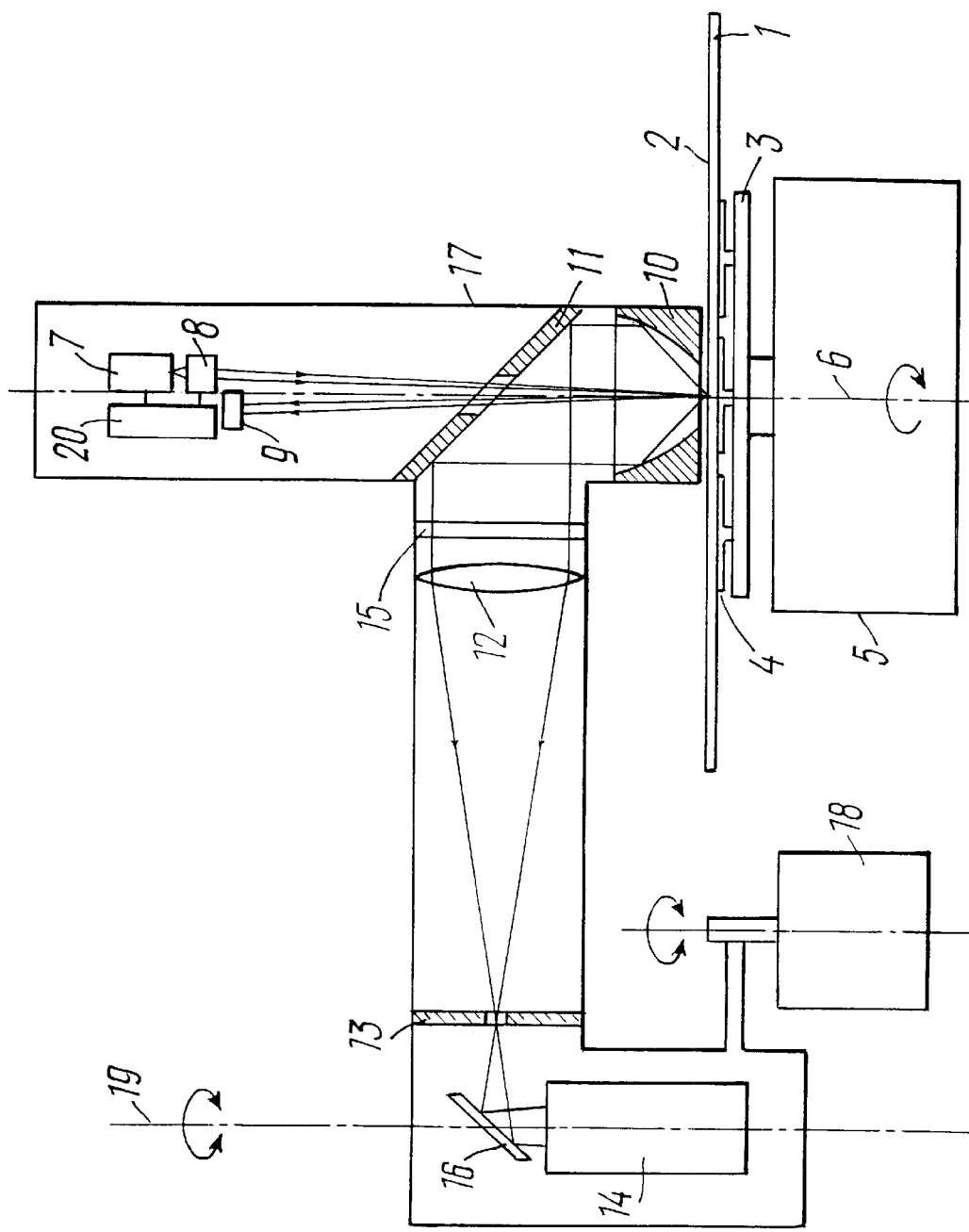
FIG. 2 illustrates a schematic diagram of another embodiment of the optical and mechanical part of the surface scanning analyzer in accordance with the present invention.

Depending on the type of the second order curve forming the body of revolution of the collecting mirror 10, a further run of beams reflected from the flat mirror 11 will be different. In the case of FIG. 2, when the collecting mirror 10 is in the form of a paraboloid of revolution, propagation lines of the light reflected therefrom are parallel. The reflection from the flat mirror 11 retains this parallelism, so the light reflected from the flat mirror 11 is collected, for the following analysis, with the collecting lens 12. The light focused by the lens passes through a diaphragm 13 and hits a second light sensing unit 14 which may be a photomultiplier and the like. In front of the collecting lens 12, the light may be transmitted through a light filter 15 to separate the light of only a required wavelength and, if appropriate, the direction of the light may be changed by means of an additional mirror 16 when the second light sensing unit 14 is mounted in a direction different from the direction toward the flat mirror 11. As to the case of FIG. 1, when the collecting mirror 10 is in the form of ellipsoid of revolution, the light reflected therefrom will be collected at the second focus of the ellipsoid. After reflecting from the flat mirror 11, the second focus will be as if turned and found on one side of the second axis of revolution (the propagation line of the light from the source 7). In so doing, there is no longer any necessity for the collecting lens 12, and the diaphragm 13 is placed just at the point of the second focus of the ellipsoid of revolution with regard to its displacement due to reflection from the flat mirror 11. Like the case when the collecting mirror 10 is in the form of paraboloid of revolution, the light filter 15 and additional mirror 16 may be used as well.

According to the present invention, the light source 7, lens 8, collecting mirror 10, flat mirror 11, first and second light sensing units 9, 14, as well as light path elements indicated by numerals 12, 13, 15 and 16 are accommodated in the housing 17 which may be light-absorbing on the inside. The housing 17 is provided with an actuator (not shown) including a rotation motor 18 (particularly, a stepper) to rotate the housing 17 about a third axis of revolution 19 which is parallel to the first axis of revolution 6 and passes outside the object 1 with the analyzed surface 2 and/or the rotary table 3.

The rotation actuator 18 enables movements of the housing 17 so that the light spot 21 (FIG. 3) formed by the light source 7 on the analyzed surface 2 is moved through an arc 22 passing through the center 23 of the analyzed surface 2 at least to one side from the center 23 of revolution up to the edge of the analyzed surface 2.

Figure 3:
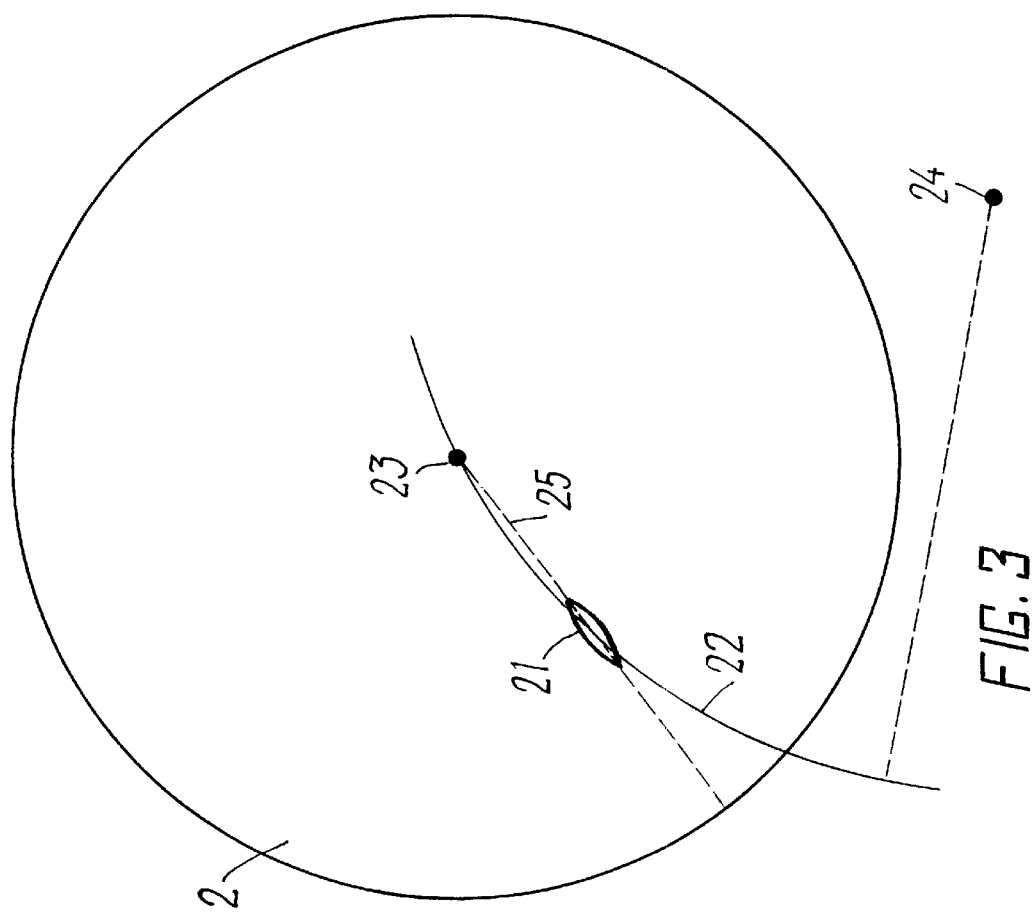
FIG. 3 shows the principle of aligning the light spot on the analyzed surface.

In such movement, the light spot 21 formed on the analyzed surface 2 and having an elongated shape will trace the arc 22 about the second center 24 of rotation (being a projection of the third axis of revolution 19 onto the plane of FIG. 3). At each point of the arc 22 the light spot 21 will be directed at some angle to the radius 25 extending from the first center 23 of rotation (being a projection of the first axis of revolution 19 onto the plane of FIG. 3) of the analyzed surface 2, which passes through this point. To provide a maximum rate of inspection of the analyzed surface 2, the optimum orientation of the light spot is to align its maximum size (the long axis of the spot) along the radius 25 passing through the point at which the light spot 21 is formed at this moment.

According to the present invention, the light spot 21 having an elongated shape on the analyzed surface 2 is aligned, at least in one predetermined position, with its maximum size along a radius 25 extending from the first center 23 of rotation. Such a predetermined position where the radius 25 crosses the arc 22 (the scanning line) may be particularly in the middle of the radius 25. It means that the light source 7 and lens 8 are mounted so as the light spot 21, when formed in the middle of the distance between the center 23 of rotation and the edge of the analyzed surface 2, is aligned with its maximum size (the long axis) exactly along the radius 25 of the analyzed surface passing through the spot 21.

However, this is not the only possibility for aligning the light spot 21. Referring to FIGS. 1 and 2, the light source 7 and lens 8 may be provided with position correction means 20. It may be, for instance, a micromotor (particularly, a stepper). In so doing, the actuator with the rotation motor 18 is provided with means (not shown) for measuring a rotation angle of the housing relative to its initial position. Then signals from the housing rotation angle measurement means, after their appropriate processing, may be fed to the position correction means 20 which will turn the light source 7 with the lens 8 so as to retain the alignment of the light spot 21 along the radius 25 extending from the first center 23 of rotation through the light spot all along the scanning line (the arc 22).

Figure 4:
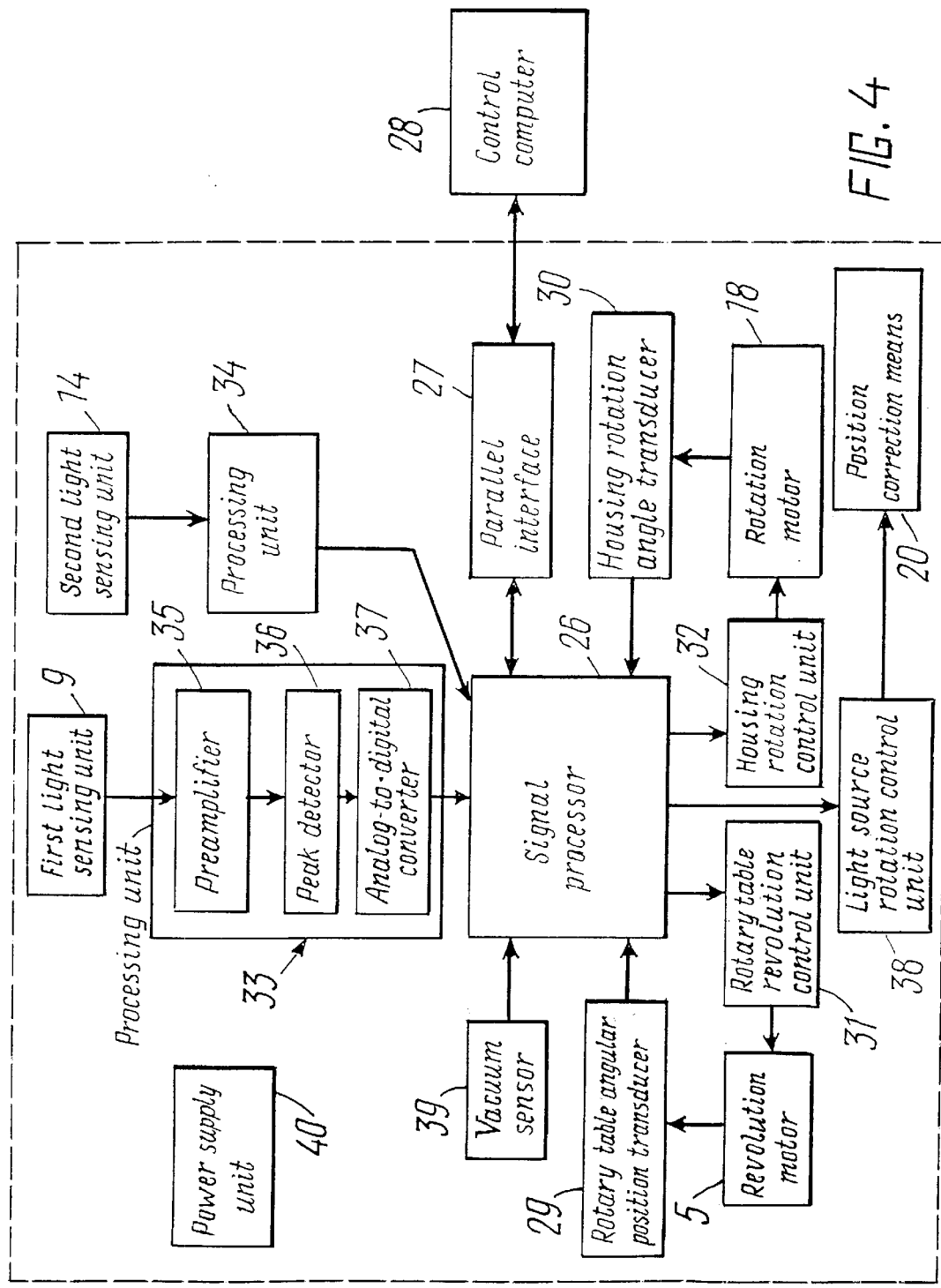
FIG. 4 shows a schematic diagram of electronic circuitry of the scanning analyzer.

The operation of the surface scanning analyzer according to the present invention may be controlled using a circuit shown in FIG. 4. The circuit is merely illustrative and serves only to confirm the practicability of the present invention.

In the circuit, a signal processor 26 is connected via a parallel interface 27 to a control computer 28 storing in its memory a program for operating the surface scanning analyzer according to the present invention. The program may be composed in accordance with the list of operations below. A parallel interface carries out the data exchange between the control computer 28 and signal processor 26 in accordance with requirements of the IEEE-1284 Standard, ensuring compatibility with the majority of computers currently in use. Inputs of the signal processor 26 are connected to a rotary table angular position transducer 29 and a housing rotation angle transducer 30 which implements in this case the above mentioned housing rotation angle measurement means. The transducers 29 and 30 are mechanically coupled to a shaft of the revolution motor 5 and to a shaft of the rotation motor 18, respectively, the motors being controlled by signals provided from corresponding signal processor outputs connected to a rotary table revolution control unit 31 and a housing rotation control unit 32, both generating signals necessary to initiate the particular motor.

The schematic diagram of FIG. 4 further shows the first 9 and second 14 light sensing units having outputs connected via respective processing units 33 and 34 to inputs of the signal processor 26. Each of the units 33 and 34 includes a preamplifier 35, a peak detector 36 and an analog-to-digital converter 37. If the first light sensing unit 9 is a light absorber (for instance, a non-reflecting surface), then the first processing unit 33 will be omitted in the diagram of FIG. 4.

The circuit in FIG. 4 may also include a light source rotation control unit 38 having inputs connected to corresponding outputs of the signal processor 26, and outputs connected to inputs of the position correction means 20 .

And lastly, the circuit in FIG. 4 includes a vacuum sensor 39 which may be used to employ the present invention in the manufacture of semiconductor wafers, and power supply unit 40 for supplying all blocks of the surface scanning analyzer in accordance with the present invention.

In operation, the surface scanning analyzer in accordance with the present invention implements the method for inspection of an analyzed surface according to the present invention in the following manner.

An object 1 with an analyzed surface 2 (for example, a silicon wafer 150, 200 or 300 mm in diameter) is mounted and fixed on the rotary table 3 by suction cups 4. On signals from corresponding control units, the motor 5 begins to revolve the rotary table 3 together with the object 1, and the actuator with the motor 18 begins to rotate the housing 17 over the analyzed surface 2 of the object 1. If the position correction means is provided, signals received thereby from the control unit induce the light source 7 with the lens 8 to turn continuously while moving through the arc 22 so as the light spot 21 formed by the light source on the analyzed surface 2 is all the time aligned with its maximum size (its long axis) along the radius 25 extending from the first center 23 of rotation through the spot. And where the position correction means 20 is not employed, the spot 21 must be set in advance with its long axis along the radius 25 in a predetermined position, for example, when the spot 21 is in the middle of the radius 25.

During the inspection, i.e. while moving the housing 17 over the revolved analyzed surface 2, the light source 7 forms through the lens 8 the light spot 21 on the analyzed surface 2 through the aperture at the center of the flat mirror 11.

If a light scattering defect exists on a microarea of the analyzed surface 2, on which the light spot 21 is formed by the light source 7, then the scattered light will hit the collecting mirror 10, the reflection from which will fall onto the flat mirror 11. The collecting mirror 10 is the form of a truncated body of revolution formed by revolving a second order curve, and is mounted so that the focus of said second order curve is at the point of forming the light spot 21. If the collecting mirror 10 is in the form of the paraboloid of revolution, the parallel light beam from the flat mirror 11, having passed through the light filter 15 and collecting lens 12, is focused in the aperture of the diaphragm 13 and hits the second light sensing unit 14, perhaps having changed again its direction at the additional mirror 16 (if the second light sensing unit 14 is a relatively bulky photomultiplier). And if the collecting mirror 10 is in the form of the ellipsoid of revolution, the light beam reflected therefrom, having been reflected from the flat mirror 11 and transmitted through the light filter 15, is collected at the "reflected" second focus of the ellipsoid of revolution (without the lens 12 which is absent in this case), with the diaphragm 13 placed at the focus, and from the diaphragm the light comes to the second light sensing unit 14. Like the case of the paraboloid, the additional mirror 16 may be used in this case as well.

A signal from the second light sensing unit 14 is provided through the processing unit 34, similar to the unit 33 or having a specific embodiment (for instance, without the preamplifier), to the signal processor, where it is used to detect the existence of a defect on the surface of the object 1. Output of the photomultiplier, as the second light sensing unit 14, is substantially a sum of two components one of which is proportional to the light scatter caused by a microroughness of the wafer surface, and the scatter in its subsurface area (the cloud effect), and the second component being caused by the presence of particles or other light-scattering defects on the surface. The signal components are separated using a software. This allows simple realisation of different measurement conditions with a relatively unsophisticated electronic circuitry of the device. Thus, in a time of scanning the wafer, a fact of presence of particles at every point of the wafer, sizes of the particles present, as well as the cloud effect of the surface are determined.

Through the parallel interface 27, data from the signal processor 26 are provided to the control computer 28 to be used in diagnostics of produced semiconductor wafers and adjustment of the process of their manufacture.

A signal from the vacuum sensor 39 is utilized by the signal processor 26 to prevent slippage of the object 1 on the rotary table 3 when vacuum in the suction cups 4 is insufficient.

The operation program of the scanning analyzer may provide for switching off the power supply unit 40 from the main blocks—motors 5 and 18, light source 7, photomultiplier of the second light sensing unit 14—in the absence of the scanning process, this reducing power consumption and increasing the lifetime.

Signals of the units 9 and 14 may be processed using any conventional algorithms (for example, as in the closest prior art). They are not the subject matter of the present invention and do not fall within the scope of the claims.

INDUSTRIAL APPLICABILITY

The present invention can be used to analyze the surface uniformity of different objects. It is particularly suitable in the semiconductor manufacturing for quality control of the semiconductor wafers processed inside the manufacturing equipment.

Although the present invention has been described in its preferable embodiments, it will be appreciated that this description is made only by way of example illustrating the main aspects of the present invention and not as a limitation to its possible realisation. Accordingly, it is intended that the appended claims be construed as encompassing all features of the invention, including the features that would be treated as equivalents.

What is claimed is:

1. A method for inspecting an analyzed surface comprising the steps of:
   (i) rotating an object with the analyzed surface about a first center of rotation;
   (ii) forming a light spot on the analyzed surface;
   (iii) moving the light spot relative to the analyzed surface through an arc about a second center of rotation which lies outside the analyzed surface;
   (iv) aligning, at least in one predetermined position, the light spot having an elongated form on the analyzed surface with its maximum size along a radius extending from the first center of rotation through the light spot; and
   (v) sensing separately a light mirror-reflected and a light scattered from the analyzed surface at the incidence point of the light spot.

2. The method according to claim 1 wherein in said predetermined position the light spot is located substantially in the middle of said analyzed surface radius extending from the first center of rotation.

3. The method according to claim 1 wherein the light spot, while being moved through said arc, is turned so as to retain its alignment along the radius extending from the first center of rotation through the light spot all along the scanning line.

4. The method according to claim 1 wherein the light scattered from the analyzed surface is collected using a system of mirrors, one of the mirrors being in the form of a truncated ellipsoid of revolution, the axis of revolution of the truncated ellipsoid of revolution substantially coinciding with the normal to the analyzed surface, erected at the incidence point of said light spot, said incidence point being at a first focus of said truncated ellipsoid of revolution, a first section plane of the truncated ellipsoid of revolution being located perpendicularly to the axis of revolution in the immediate proximity to said first focus, and a second section plane being parallel to the first section plane, and another mirror being a flat mirror having an aperture at the center, arranged at an angle to the axis of revolution of the truncated ellipsoid of revolution, and intended for passing therethrough the light from the light source to the analyzed surface and the light mirror-reflected therefrom, and for reflecting the light scattered from the analyzed surface and reflected from the collecting mirror, wherein the light reflected from the flat mirror is transmitted through a light filter and then diaphragmed at a point corresponding to a second focus of said ellipsoid of revolution with regard to reflection from said flat mirror.

5. The method according to claim 1 wherein the light scattered from the analyzed surface is collected using a system of mirrors, one of the mirrors being in the form of a truncated paraboloid of revolution having an axis of revolution substantially coinciding with the normal to the analyzed surface erected at the incidence point of said light spot, said incidence point being at the focus of said truncated paraboloid of revolution, a first section plane of the truncated paraboloid of revolution being located perpendicularly to the axis of revolution in the immediate proximity to said focus, and a second section plane being parallel to the first section plane, and another mirror being a flat mirror having an aperture at its center, arranged at an angle to the axis of revolution of the truncated paraboloid of revolution, and intended for passing therethrough the light from the light source to the analyzed surface and the light mirror-reflected therefrom, and for reflecting the light scattered from the analyzed surface and reflected from the collecting mirror, wherein the light reflected from the flat mirror is transmitted through a light filter, collected by a lens and then diaphragmed at the point of the lens focus.

6. A surface scanning analyzer comprising:

(i) a rotary table for mounting thereon and rotating an object with an analyzed surface about a first axis of revolution that is perpendicular to the analyzed surface;

(ii) a light source for illuminating the analyzed surface by a light spot at an angle close to the normal to the analyzed surface;

(iii) a collecting mirror in the form of a truncated body of revolution formed by revolving a second order curve about a second axis of revolution which is parallel to the first axis of revolution and substantially coincides with the normal to the analyzed surface erected at the incidence point of said light spot, said incidence point being at the focus of said truncated body of revolution, a first section plane of the truncated body of revolution being located perpendicularly to the second axis of revolution in the immediate proximity to said focus, and a second section plane being parallel to the first section plane;

(iv) a first light sensing unit for sensing the light mirror-reflected from the analyzed surface, said first light sensing unit being located close to the light source;

(v) a second light sensing unit for sensing the light scattered from the analyzed surface and reflected from the collecting mirror;

(vi) a flat mirror having an aperture at the center, arranged at an angle to the second axis of revolution and intended for passing therethrough the light from the light source to the analyzed surface and the light mirror-reflected from the analyzed surface to the first light sensing unit and for reflecting the light from the collecting mirror to the second light sensing unit; wherein the light source, collecting mirror, flat mirror with the aperture, and first and second light sensing units are accommodated in a housing rotatable about a third axis of revolution which is parallel to the first axis of revolution and passes outside the object with the analyzed surface and/or the rotary table;

the light source being mounted so as said light spot having an elongated form on the analyzed surface is aligned, at least in one predetermined position of the housing, with its maximum size along a radius extending from the center of rotation of the analyzed surface.

7. The analyzer according to claim 6 wherein the first light sensing unit is a light absorber.

8. The analyzer according to claim 6 wherein the first light sensing unit is intended for determining non-scattering defects on the analyzed surface.

9. The analyzer according to claim 6 wherein the second light sensing unit is intended for sensing the light reflected from the flat mirror.

10. The analyzer according to claim 6 wherein the body of revolution of the collecting mirror is an ellipsoid of revolution having a diaphragm placed at the second focus of the ellipsoid of revolution with regard of reflection from the flat mirror to pass therethrough the light reflected from the flat mirror to the second light sensing unit.

11. The analyzer according to claim 10 wherein a light filter is mounted between the flat mirror and the diaphragm.

12. The analyzer according to claim 6 wherein the body of revolution of the collecting mirror is a paraboloid of revolution, and a collecting lens and a diaphragm are mounted between the flat mirror and the second light sensing unit, for collecting and passing the light mirrored from the flat mirror to the second light sensing unit.

13. The analyzer according to claim 12 wherein a light filter is mounted between the flat mirror and the collecting lens.

14. The analyzer according to claim 6 further comprising a housing rotation actuator to move the housing over the analyzed surface at least to one side from the center of rotation of the analyzed surface.

15. The analyzer according to claim 14 wherein in said predetermined position of the housing, said light spot is located substantially in the middle of said analyzed surface radius extending from the center of rotation of the analyzed surface.

16. The analyzer according to claim 14 wherein the housing rotation actuator is provided with housing rotation angle measurement means, and the light source is provided with position correction means for turning the light source in accordance with signals from the rotation angle measurement means to enable said aligning of the light spot along the radius extending from the center of rotation of the analyzed surface all along the scanning line.

17. The analyzer according to claim 6 wherein the housing is light-absorbing on the inside.

18. The analyzer according to claim 6 wherein the rotary table is provided with three suction cups located symmetrically about the first axis of revolution and intended for mounting the object with the analyzed surface on the rotary table.

* * * * *